United States Patent [19]

Hu

[11] Patent Number: 5,561,695
[45] Date of Patent: Oct. 1, 1996

[54] METHODS AND APPARATUS FOR REDUCING IMAGE ARTIFACTS

[75] Inventor: Hui Hu, Waukesha, Wis.

[73] Assignee: General Electric Company, Milwaukee, Wis.

[21] Appl. No.: 556,252

[22] Filed: Nov. 13, 1995

[51] Int. Cl.$^6$ ......................................... A61B 6/03
[52] U.S. Cl. ............................... 378/8; 378/15; 378/901
[58] Field of Search ......................... 364/413.14, 413.19; 378/8, 15, 901

[56] References Cited

U.S. PATENT DOCUMENTS 5,396,418  3/1995  Heuscher ........................... 364/413.18
5,400,377  3/1995  Hu et al. ........................................... 378/8
5,473,655  12/1995  Hu ..................................................... 378/4

Primary Examiner—David P. Porta
Assistant Examiner—David Vernon Bruce
Attorney, Agent, or Firm—John S. Beulick; John H. Pilarski

[57] ABSTRACT

The present invention, in one form, is a method for improving image quality in CT helical scan systems by using a post reconstruction filtering algorithm. In accordance with one embodiment of the algorithm, image data is segmented into sharp structure data and background data. The background data is then filtered to remove reconstruction and data artifacts. The filtered background data is then combined with the sharp structure data. The combined data can then be used to generate an artifact reduced image.

12 Claims, 2 Drawing Sheets

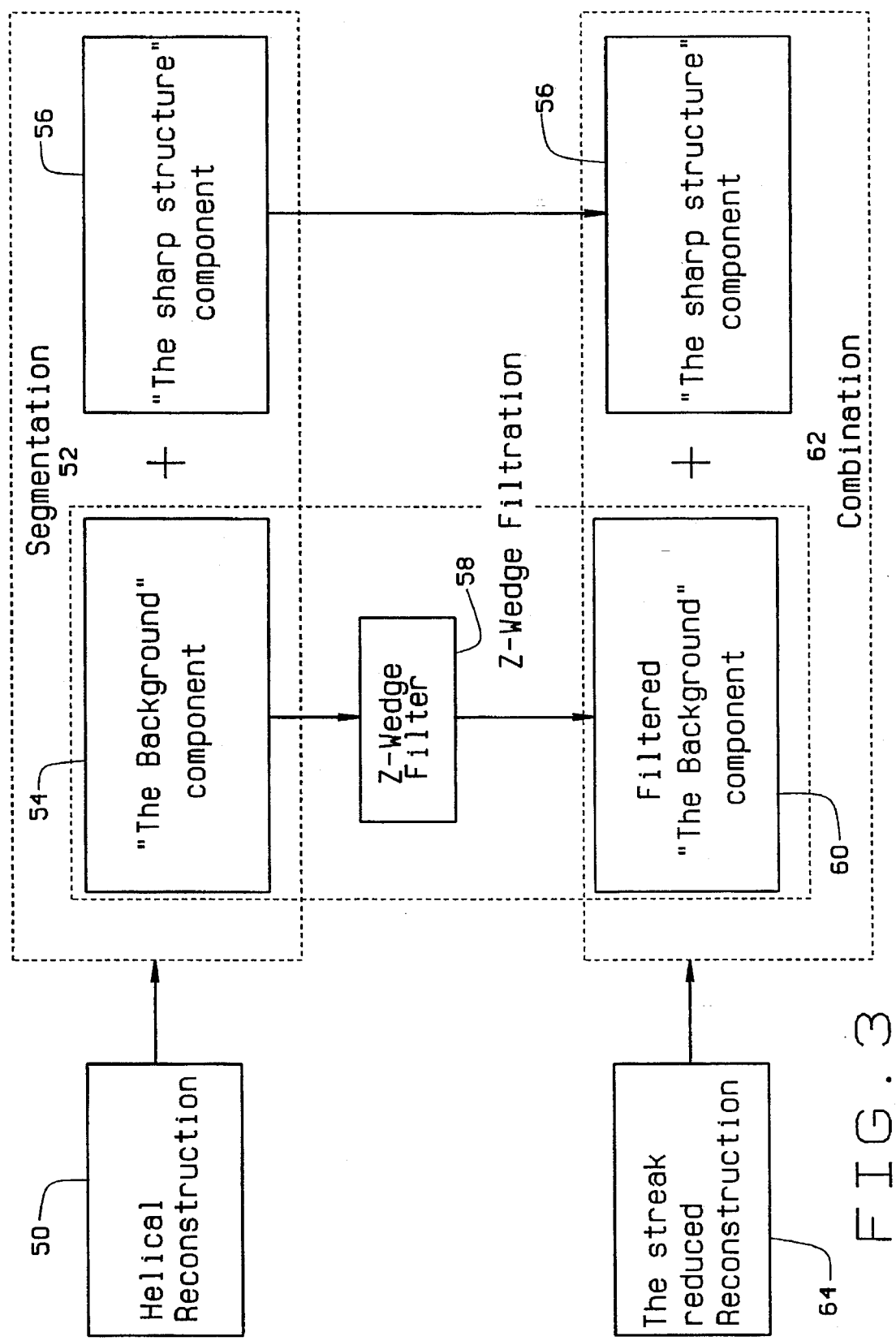

METHODS AND APPARATUS FOR REDUCING IMAGE ARTIFACTS

FIELD OF THE INVENTION

This invention relates generally to computed tomography (CT) imaging and more particularly, to reducing image artifacts in an image reconstructed from helical scan data.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are described in C. Crawford and K. King, "Computed Tomography Scanning with Simultaneous Patient Translation", Med. Phys. 17(6), Nov/Dec 1990, and in U.S. patent application Ser. No. 08/362,247, Helical Interpolative Algorithm For Image Reconstruction in A CT System, filed Dec. 22, 1994 and assigned to the present assignee.

When reconstructing an image for a particular slice, as the distance between the slice location and the location where the actual projection data was collected increases, the amount of error in the generated data for that slice also increases. These errors in the projection data usually causes low frequency shading artifacts. In sagittal or coronal image reformatting, these errors also cause fine horizontal streaks or artifacts. As with streak artifacts in axial imaging, the streaks in the reformatted images are annoying.

Since the projection data errors generally propagate in the horizontal (backprojection) direction, the streak artifacts have no correlation from slice to slice. That is, the artifacts are of high frequency in the z direction. Such artifacts can be removed by filtering the data in the z direction, however, when the true structure has rapid changes in the z direction, such as tissue air interfaces or bone-tissue interfaces, simply filtering the data in the z direction will result in a loss of image resolution.

It is desirable, of course, to reduce reconstruction artifacts. It also is desirable to reduce such reconstruction artifacts without adversely affecting image resolution.

SUMMARY OF THE INVENTION

These and other objects may be attained by methods and apparatus which remove horizontal streaks of an image reconstructed using helical scan data without reducing image resolution. In accordance with one embodiment, helical reconstruction is performed to generate image data. The image data is then filtered to remove the horizontal streaks. Such filtering is performed by segmenting the image data into two components. One component is referred to as the background component and the other component is referred to as the sharp structure component. Such segmentation can be performed using grey-scale thresholding.

After the image data is segmented as described above, the background component image data is filtered using a z-wedge filter. Since such background data contains most of the artifacts caused by errors in the helical projection data, such filtering substantially removes the Fourier spectrum corresponding to the streaks. The filtered background data is then combined with the sharp structure data to provide a complete set of image data, corresponding to an image with fewer artifacts. Using the above-described algorithm, reconstruction artifacts, such as horizontal streaks, are reduced. In addition, the image resolution is maintained.

BRIEF DESCRIPTION OF THE DRAWINGS

FIG. 3 illustrates a sequence of steps executed in accordance with one embodiment of the present invention.

DETAILED DESCRIPTION OF THE DRAWINGS

Figure 1:
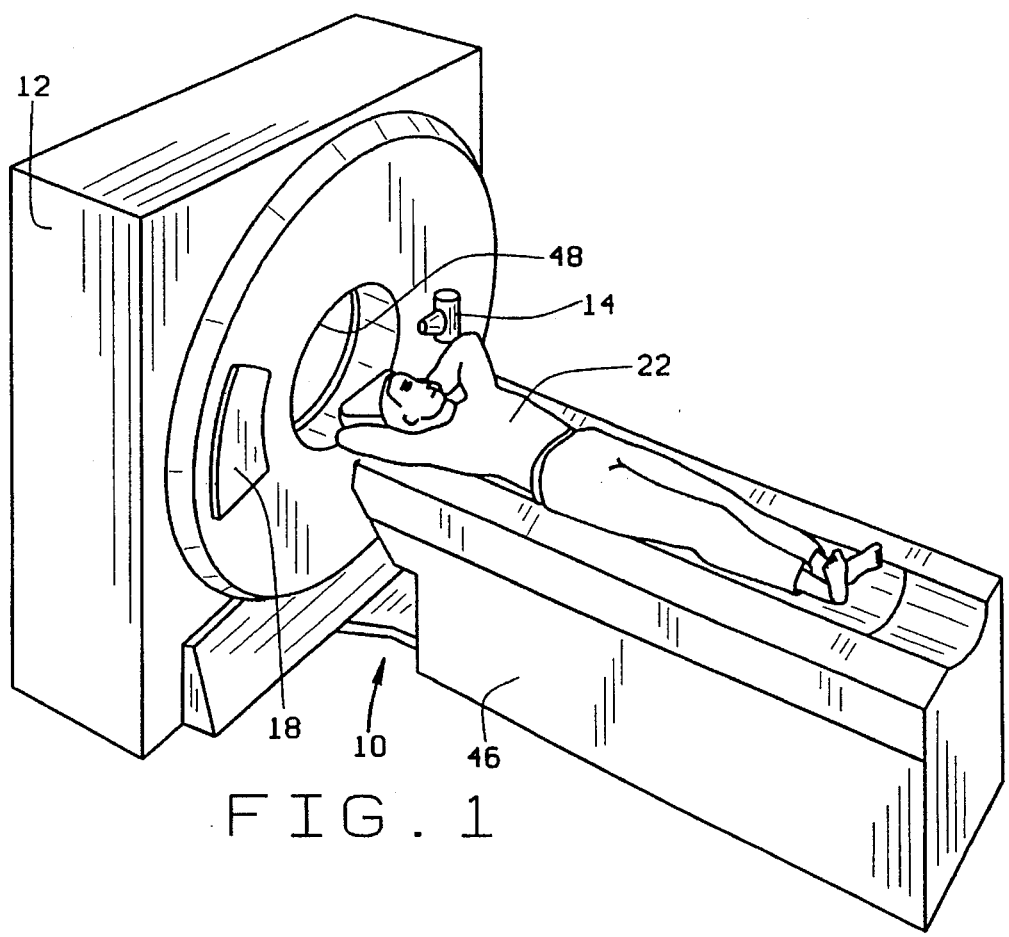
FIG. 1 is a pictorial view of a CT imaging system.
Figure 2:
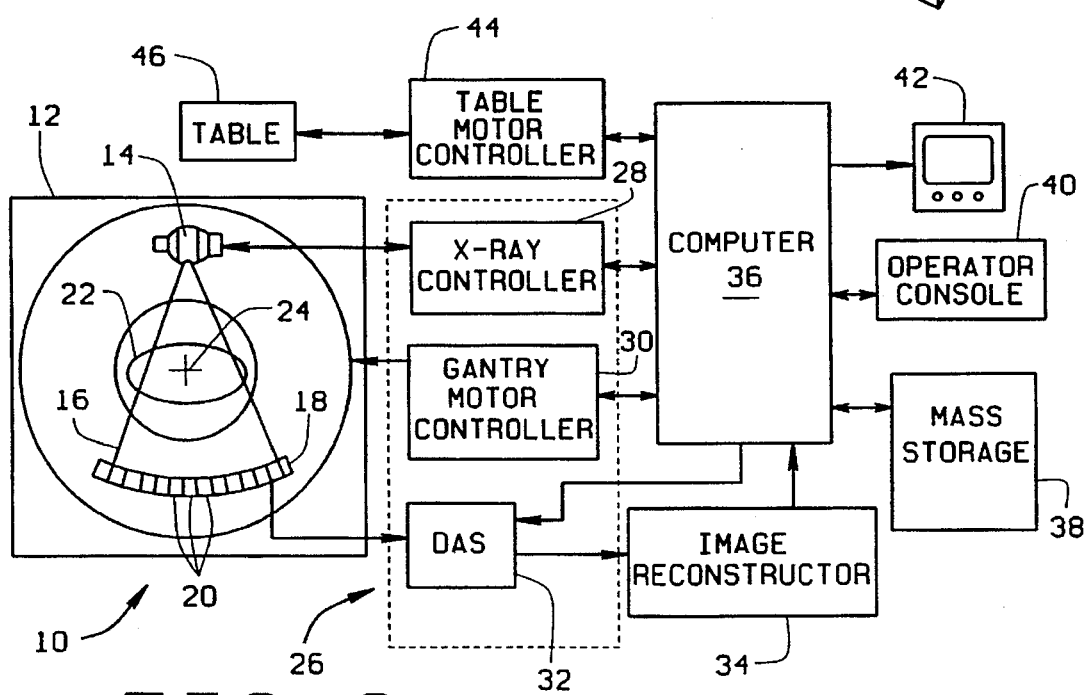
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion which describes reducing image artifacts sometimes refers specifically to sagittal and coronal images. The artifact reduction algorithm, however, is not limited to practice in connection with only sagittal and coronal images and may be used with other images as well. It should be further understood that the algorithm would be implemented in computer 36 and would process, for example, image data stored in mass storage 38. Alternatively, the algorithm could be implemented in image reconstructor 34 and supply filtered image data to computer 36. Other alternative implementations are, of course, possible.

With respect to FIG. 3, and as described above, in performing a CT scan, projection data is obtained. In helical scanning, helical reconstruction 50 is then performed to generate image data. With respect to image reconstruction, many image reconstruction algorithms are known and some of the known algorithms are implemented in commercially available CT machines. The present algorithm could be implemented in connection with many of such reconstruction algorithms and is not directed to, nor limited to practice with, any one particular image reconstruction algorithm.

Referring specifically to FIG. 3, subsequent to helical reconstruction, the resulting image data is segmented 52 into two segments. Specifically, a background component 54 and sharp structure component 56 are generated. This segmentation is performed, in one embodiment, using grey-scale thresholding. Grey-scale thresholding refers to the process of comparing CT numbers with a predetermined range, i.e., a threshold, and assigning each CT number to a particular component based on whether the respective CT number is above or below the threshold. Further details regarding grey-scale thresholding are set forth in U.S. Pat. No. 5,400,377, Artifact Reduction Method For Tomographic Image Reconstruction Using Cross-Plane Rays, which is assigned to the present assignee and hereby incorporated herein, in its entirety, by reference.

For example, when an object of interest has rapid changes in its structure along the z-direction, the CT numbers for the structure usually differ from the CT numbers for the image background by a large margin. Since the CT numbers, or grey-scales, are different for the rapidly changing, or sharp structure and the background, grey-scale thresholding is effective for segmenting the image data into background and sharp structure components.

After segmenting the image data as described above, the background image data or component is filtered 58 using a z-wedge filter. Further details regarding z-wedge filtering are set forth in the above referenced U.S. Pat. No. 5,400,377.

Filtered background image data 60 is then combined 62 with sharp structure image data or component 56. The combined data can then be used to generate an image 64 having few horizontal streaks.

The z-wedge filter, as noted above, removes the high frequency artifacts in the z-direction from the background component. However, by segmenting the sharp structure component before filtering, image resolution is maintained. Therefore, horizontal streaks and artifacts are reduced while preserving image resolution.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the CT system described herein is a "third generation" system, many other systems, such as "fourth generation" systems may be used. In addition, the z-wedge filter may not be necessary for all applications. Performing simple low pass filtering along the z direction may be sufficient for some applications. Accordingly, the spirit and scope of the invention are to be limited only by the terms of the appended claims.

What is claimed is:

1. A method for reducing artifacts in image data generated from projection scan data collected in a helical scan, said method comprising the steps of:

segmenting the image data into background image data and sharp structure image data;

filtering the background image data; and combining the filtered background image data and the sharp structure image data.

2. A method in accordance with claim 1 wherein segmenting the image data into background image data and sharp structure image data is performed using grey-scale thresholding.

3. A method in accordance in claim 1 wherein filtering the background image data is performed using a z-wedge filter.

4. A method in accordance with claim 1 wherein combining the filtered background image data and sharp structure image data comprises the step of adding the filtered background image data to the sharp structure image data.

5. Apparatus for reducing artifacts in image data generated from projection scan data collected in a helical scan, said apparatus comprising:

means for segmenting the image data into background image data and sharp structure data;

means for filtering the background image data; and means for combining the filtered background image data and the sharp structure image data.

6. Apparatus in accordance with claim 5 wherein said means for segmenting image data comprises a computer programmed to segment the image data based on grey-scale thresholding.

7. Apparatus in accordance with claim 5 wherein said means for filtering the background image data comprises a computer programmed to filter the image data using a z-wedge filter.

8. Apparatus in accordance with claim 5 said means for combining the filtered background image data and the sharp structure data comprises a computer programmed to add the filtered background image data to the sharp structure image data.

9. A system for reducing artifacts in image data generated from projection scan data collected in a helical scan, said system configured to:

segment the image data into background image data and sharp structure image data;

filter the background image data; and combine the filtered background image data and the sharp structure image data.

10. A system in accordance with claim 9 wherein said system is configured to segment the image data into background image data and sharp structure image data by using grey-scale thresholding.

11. A system in accordance in claim 9 wherein said system is configured to filter the background image data by using a z-wedge filter.

12. A system in accordance with claim 9 wherein said system is configured to combine the filtered background image data and sharp structure image data by adding the filtered background image data to the sharp structure image data.

* * * * *